US008283371B2

(12) United States Patent
Wadman (10) Patent No.: US 8,283,371 B2
(45) Date of Patent: Oct. 9, 2012

(54) COMPOUNDS

(75) Inventor: Sjoerd Nicolaas Wadman, Welwyn Garden City (GB)

(73) Assignee: Novacta Biosystems Limited, Hertfordshire (GB)

( * ) Notice: Subject to any disclaimer, the term of this patent is extended or adjusted under 35 U.S.C. 154(b) by 0 days.

(21) Appl. No.: 12/686,135

(22) Filed: Jan. 12, 2010

(65) Prior Publication Data

US 2010/0179207 A1     Jul. 15, 2010

Related U.S. Application Data

(60) Provisional application No. 61/144,490, filed on Jan. 14, 2009.

(51) Int. Cl.
*A61K 31/40* (2006.01)
(52) U.S. Cl. ........................................ 514/414
(58) Field of Classification Search ............... None
See application file for complete search history.

(56) References Cited

U.S. PATENT DOCUMENTS

| 3,710,795 A | 1/1973 | Higuchi et al. |
| 5,112,806 A | 5/1992 | Chatterjee et al. |
| 5,304,540 A | 4/1994 | Blackburn et al. |
| 5,667,991 A | 9/1997 | Koller et al. |
| 5,683,675 A | 11/1997 | Molina y Vedia et al. |
| 5,763,395 A | 6/1998 | Blackburn et al. |
| 5,958,873 A | 9/1999 | Sakr et al. |
| 5,985,823 A | 11/1999 | Goldstein |
| 6,022,851 A | 2/2000 | Vertesy et al. |
| 6,569,830 B1 | 5/2003 | Climo et al. |
| 7,122,514 B2 | 10/2006 | Climo et al. |
| 2010/0168410 A1 | 7/2010 | Cade et al. |

FOREIGN PATENT DOCUMENTS

| DE | 197 45 583 | 4/1999 |
| EP | 0195359 | 9/1986 |
| EP | 0572942 | 12/1993 |
| EP | 0700998 | 3/1996 |
| EP | 1646646 | 3/2007 |
| WO | WO 91/07949 | 6/1991 |
| WO | WO 91/11172 | 8/1991 |
| WO | WO 94/02518 | 2/1994 |
| WO | WO 97/00694 | 1/1997 |
| WO | WO 98/55148 | 12/1998 |
| WO | WO 02/00196 | 1/2002 |
| WO | WO 02/088367 | 11/2002 |
| WO | WO 02/103010 | 12/2002 |
| WO | WO 03/099862 | 12/2003 |
| WO | WO 2004/033706 | 4/2004 |
| WO | WO 2005/093069 | 10/2005 |
| WO | WO 2006/080920 | 8/2006 |
| WO | WO 2007/036706 | 4/2007 |
| WO | WO 2007/083112 | * 7/2007 |
| WO | WO 2008/151434 | 12/2008 |
| WO | WO 2009/010763 | 1/2009 |
| WO | WO 2009/010765 | 1/2009 |
| WO | WO 2010/058238 | 5/2010 |
| WO | WO 2010/082018 | 7/2010 |
| WO | WO 2010/082019 | 7/2010 |
| WO | WO 2010/089544 | 8/2010 |

OTHER PUBLICATIONS

Malabarba et al (J Antibiotics, 43:1089-1097, 1990).*
Han (Advances in Characterization of Pharmaceutical Hydrates. Trends in Bio/Pharmaceutical Industry, pp. 25-29. Mar. 2006).*
Vippagunta et al (Adv Drug Deliv Rev 48:3-26, 2001).*
Altena et al. "Biosynthesis of the lantibiotic mersacidin: organization of a type B lantibiotic gene cluster" Applied and Environmental Microbiology 66(6): 2565-2571 (2000).
Arioli et al. "Gardimycin, a new anitbiotic from *Actinoplanes*: III. Biological properties" The Journal of Antibiotics 29(5):511-515 (1976).
Berge et al. "Pharmaceutical salts" Journal of Pharmaceutical Sciences 66(1):1-19 (1977).
Bierbaum et al. "Cloning, sequencing and production of the lantibiotic mersacidin" FEMS Microbiology Letters 127:121-126 (1995).
Bierman et al. "Plasmid cloning vectors for the conjugal transfer of DNA from *Escherichia coli* to *Streptomyces* spp." Gene 116(1):43-49 (1992).
Britton et al. "Genome-Wide Analysis of the Stationary-Phase Sigma Factor (Sigma-H) Regulon of *Bacillus subtilis*" Journal of Bacteriology 184(17):4881-4890 (2002).
Castiglione et al. "A novel lantibiotic acting on bacterial cell wall synthesis produced by uncommon actinomycete *Planomonospora* sp." Biochemistry 46:5884-5895 (2007).
Chatterjee et al. "Biosynthesis and Mode of Action of Lantibiotics" Chem. Rev. 105:633-683 (2005).
Coronelli et al. "Gardimycin, A New Antibiotic From Actinoplanes: II. Isolation and preliminary characterization" Journal of Antibiotics 29(5):507-510 (1976).
Cotter et al. "Bacterial lantibiotics: strategies to improve therapeutic potential" Current Protein Peptide Science 6(1):61-75 (2005).
Dabard et al. "Ruminococcin A, a new lantibiotic produced by a *Ruminococcus gnavus* strain isolated from human feces" Appl. Environ. Microbiol. 67:4111-4118 (2001).
Dawson "Lantibiotics as antimicrobial agents" Expert Opinion on Therapeutic Patents, Informa Healthcare, GB, 17(4):365-369 (2007).
de Vos et al. "Maturation pathway of nisin and other lantibiotics: post-translationally modified antimicrobial peptides exported by gram-positive bacteria" Molecular Microbiology 17(3):427-37 (1995).
Dower et al. "High efficiency transformation of *E. coli* by high voltage electroporation" Nucleic Acids Research 16(13):6127-6145 (1988).
Fleisher et al. "Improved oral drug delivery: solubility limitations overcome by the use of prodrugs" Advanced Drug Delivery Reviews 19(2):115-130 (1996).
Flett et al. "High efficiency intergeneric conjugal transfer of plasmid DNA from *Escherichia coli* to methyl DNA-restricting Streptomycetes" FEMS Microbiology Letters 155(2): 223-229 (1997).

(Continued)

*Primary Examiner* — Craig Ricci
(74) *Attorney, Agent, or Firm* — Morgan, Lewis & Bockius LLP (57) ABSTRACT

The present invention pertains generally to certain compounds of the deoxyactagardine A and B type. Such compounds are suitable for use in the treatment of microbial infections, for example *Clostridium* infection, such as *C. perfringens, C. difficile, C. tetani*, and/or *C. botulinum*, in particular *C. difficile*, especially infection of the colon and/or lower intestines and diarrhea associated with the microbial infection.

4 Claims, 7 Drawing Sheets

OTHER PUBLICATIONS

Fukase et al. "Synthetic study of peptide antibiotic nisin. V. Total synthesis of nisin" Bull. Chem. Soc. Jpn. 65:2227-2240 (1992).

Fumi et al. "Rifaximin treatment for symptoms of irritable bowel syndrome" The Annals of Pharmacotherapy 42:408-412 (2008).

Gardiner et al. "Fate of the Two-Component Lantibiotic Lacticin 3147 in the Gastrointestinal Tract" Applied and Environmental Microbiology 73(21):7103-7109 (2007).

Gravesen et al. "pbp2229-Mediated nisin resistance mechanism in *Listeria monocytogenes* confers cross-protection to class IIa bacteriocins and affects virulence gene expression" Applied and Environmental Microbiology 70(3): 1669-1679 (2004).

Guder et al. "Role of the single regulator MrsR1 and the two-component system MrsR2/K2 in the regulation of mersacidin production and immunity" Applied and Environmental Microbiology 68(1):106-113 (2002).

Guiotto et al. "PEGylation of the antimicrobial peptide nisin A: problems and perspectives" Il Farmaco 58(1):45-50 (2003).

Gust et al. "PCR-targeted Streptomyces gene replacement identifies a protein domain needed for biosynthesis of the sesquiterpene soil odor geosmin" PNAS 100(4): 1541-1546 (2003).

Gust et al. "λ, Red-mediated genetic manipulation of antibiotic-producing Streptomyces" Advances in Applied Microbiology 54:107-128 (2004).

Heinzelmann et al. "A glutamate mutase is involved in the biosynthesis of the lipopeptide antibiotic friulimicin in Actinoplanes friuliensis" Antimicrobial Agents and Chemotherapy 47(2): 447-457 (2003).

Hilger et al. "Differential binding of IgG and IgA antibodies to antigenic determinants of bovine serum albumin" Clin. Exp. Immunol 123:387-394 (2001).

Holtsmark, et al. "Purification, Characterization, and Gene Sequence of Michiganin A, an Actagardine-Like Lantibiotic Produced by the Tomato Pathogen *Clavibacter michiganensis* subsp. *michiganensis*" Applied and Environmental Microbiology 72(9):5814-5821 (2006).

Jack et al. "The genetics of lantibiotic biosynthesis" BioEssays 17(9): 793-802 (1995).

Kettenring et al. "Sequence determination of actagardine, a novel lantibiotic, by homonuclear 2D NMR spectroscopy" J. Antibiot. 43(9):1082-1088 (1990).

Lonetto et al. "The sigma 70 family: sequence conservation and evolutionary relationships" Journal of Bacteriology 174(12): 3843-3849 (1992).

Louie et al. "A phase 2 study of the toxin binding polymer tolevamer in patients with C. difficile associated diarrhoea" Proceedings of 14th European Congress of Clinical Microbiology and Infectious Diseases, Prague Congress Centre, Prague, Czech Republic, P548 (May 1-4, 2004).

Louie et al. "Tolemaver (GT160-246) binds Clostridium cytotoxins A/B and is associated with restoration of components of the anaerobic intestinal microflora during treatment of C. difficileassociated diarrhoea" Proceedings of 14th European Congress of Clinical Microbiology and Infectious Diseases, Prague Congress Centre, Prague, Czech Republic, P855 (May 1-4, 2004).

Malabarba et al. "Physico-chemical and biological properties of actagardine and some acid hydrolysis products" The Journal of Antibiotics 38(11):1506-1511 (1985).

Malabarba et al. "Synthesis and biological activity of some amide derivatives of the lantibiotic actagardine" The Journal of Antibiotics 43(9):1089-1097 (1990).

Marahiel et al. "Regulation of peptide antibiotic production in Bacillus" Molecular Microbiology 7(5):631-636 (1993).

McClerren et al. "Discovery and in vitro biosynthesis of haloduracin, a two-component lantibiotic"PNAS 103(46):17243-17248 (2006).

Miner et al. "Steroid-refractory ulcerative colitis treated with corticosteroids, metronidazole and vancomycin: a case report" BMC Gastroenterology 5:3 (2005).

O'Sullivan et al. "High- and low-copy-number Lactococcus shuttle cloning vectors with features for clone screening" Gene 137:227-231 (1993).

Parenti et al. "Gardimycin, a new antibiotic from Actinoplanes. I. Description of the producer strain and fermentation studies" The Journal of Antibiotics 29(5):501-506 (1976).

Rea et al. "Antimicrobial activity of lacticin 3147 against clinical Clostridium difficile strains" Journal of Medical Microbiology 56:940-946 (2007).

Rey et al. "Complete genome sequence of the industrial bacterium *Bacillus licheniformis* and comparisons with closely related *Bacillus* species" Genome Biology 5(10):R77 (2004).

Sahl et al. "Lantibiotics: Biosynthesis and biological activities of uniquely modified peptides from gram-positive bacteria" Ann. Rev. Microbiology 52:41-79 (1998).

Somma et al. "Gardimycin, a new antibiotic inhibiting peptidoglycan synthesis" Antimicrobial Agents and Chemotherapy 11(3):396-401 (1977).

Szekat et al. "Construction of an expression system for site-directed mutagenesis of the lantibiotic mersacidin" Applied and Environmental Microbiology 69(7):3777-3783 (2003).

"Treatment of Clostridium difficile—Associated Disease (CDAD)" Obstetrics and Gynecology 109(4):993-995 (2007).

Turner et al. "Solution structure of plantaricin C, a novel lantibiotic" Eur. J. Biochem. 264:833-839, (1999).

Turtell et al. "The use of nisin in cheesemaking. Chapter 5: International acceptance of nisin as a food preservative" Bulletin of the Int. Dairy Fed. 329:20-23 (1988).

Ugurlu et al. "Colonic delivery of compression coated nisin tablets using pectin/HPMC polymer mixture" Eur. J. Pharm. Biopharm. 67:202-210 (2007).

van Kraaij et al. "Lantibiotics: biosynthesis, mode of action and applications" Nat. Prod. Rep. 16:575-587 (1999).

Vértesy et al. "Ala(0)-actagardine, a new lantibiotic from cultures of Actinoplanes liguriae ATCC 31048" Journal of Antibiotics (Tokyo) 52(8):730-741 (1999).

Zimmermann et al. "The tetracyclic lantibiotic actagardine. 1H-NMR and 13C-NMR assignments and revised primary structure" Eur. J. Biochem. 228:786-797 (1995).

Zimmermann et al. "The three-dimensional solution structure of the lantibiotic murein-biosynthesis-inhibitor actagardine determined by NMR" Eur. J. Biochem. 246:809-819 (1997).

Appleyard et al. "NVB302 : Gastrointestinal Stability and in vivo Activity in the Hamster Cecitis Model for Clostridium difficile Infection," Poster F1-1520, 49th ICAAC, Sep. 12-15, 2009, San Francisco, USA.

Appleyard et al. "NVB302: A Narrow Spectrum Antibiotic under Development for the Treatment of Clostridium difficile Infection," Poster F1-1517, 49th ICAAC, Sep. 12-15, 2009, San Francisco, USA.

Berendsen, "A Glimpse of the Holy Grail?" Science, 1998, 282, pp. 642-643.

Boakes et al., "Organization of the genes encoding the biosynthesis of actagardine and engineering of a variant generation system," Molecular Microbiology, 2009, 72(5), pp. 1126-1136.

Bradley et al. "Limits of Cooperativity in a Structurally Modular Protein: Response of the Notch Ankyrin Domain to Analogous Alanine Substitutions in Each Repeat," J. Mol. Biol., 2002, 324, pp. 373-386.

Definition of moiety, from http://dictionary.reference.com/browse/moiety, pp. 1-3. Accessed Aug. 26, 2010.

Designing Custom Peptides, from SIGMA Genosys, pp. 1-2. Accessed Dec. 16, 2004.

European Examination for European Patent Application No. 07704921.1 dated Aug. 30, 2010.

International Search Report and Written Opinion for PCT/GB2010/000042 dated May 20, 2010.

International Search Report and Written Opinion for PCT/GB2010/000188 dated May 20, 2010.

New Zealand Examination Report on New Zealand Patent Application 569486 dated Apr. 27, 2010.

Ngo et al. "Computational Complexity, Protein Structure Prediction, and the Levinthal Paradox," The Protein Folding Problem and Tertiary Structure Prediction, K. Merc Jr. and S. Le Grand Edition, 1994, pp. 491-495.

Rudinger J, "Characteristics of the amino acids as components of a peptide hormone sequence," Peptide Hormones, JA Parsons Edition, University Park Press, Jun. 1976, pp. 1-7.

Schinzel R, Drueckes P, "The phosphate recognition site of *Escherichia coli* maltodextrin phosphorylase," FEBS, Jul. 1991, 286(1,2), pp. 125-128.

Translation of Israeli Examination Report on Israeli Patent Application No. 192446 dated Apr. 22, 2010.

Voet et al. "Abnormal Hemoglobins," Biochemistry, Second Edition, John Wiley & Sons, Inc., 1995, pp. 235-241.

Wadman et al. "NVB302: In vitro Activity Against Clostridium difficile and Intestinal Strains of Anaerobic Bacteria," Poster F1-1518, 49th ICAAC, Sep. 12-15, 2009, San Francisco, USA.

European Search Report issued in European Patent Application No. EP 10 00 0424 (Apr. 1, 2010).

European Examination issued in European Patent Application No. 07 704 921.1 (Apr. 4, 2010).

International Search Report and Written Opinion in PCT/GB2010/000043 (Mar. 29, 2010).

Widdick et al., "Cloning and engineering of the cinnamycin biosynthetic gene cluster from *Streptomyces cinnamoneus cinnamoneus* DSM 40005", PNAS, 100(7):4316-4321 (Apr. 1, 2003).

Written Opinion of the International Preliminary Examining Authority in PCT/GB2010/000043, dated Feb. 1, 2011.

Wikipedia, the free encyclopedia, "Lanthionine", http://en.wikipedia.org/wiki/Lanthionine, Nov. 2, 2011.

Office Action issued in a related European Patent Application No. 10700336.0, dated May 3, 2012.

Office Action issued in a related European Patent Application No. 10702536.3, dated May 11, 2012.

\* cited by examiner

Figure 5 HPLC chromatogram of Example 1 reaction mixture

Figure 6 HPLC chromatogram of Example 1 post C18 Bond Elut

Figure 7 HPLC chromatogram of flash purified compound of Example 1

COMPOUNDS

This application claims the benefit of U.S. Provisional Application No. 61/144,490, filed Jan. 14, 2009, which is herein incorporated by reference in its entirety.

The present invention relates to certain novel compounds, pharmaceutical compositions comprising same and use of the compounds and compositions for the treatment of microbial infections particularly *C. difficile* infection, especially in the colon and/or lower intestines.

Many antibiotic compounds have been identified from natural sources including microorganisms. Often the antibiotic compounds have a complicated chemical structure and in particular a complicated stereochemical structure.

Recently a new chemical series of antibiotics was identified, in WO 2007/083112, based on deoxyactagardine B. Deoxyactagardine B is synthesised by a bacterium *Actinoplanes liguriae* and it and a number of its derivatives show promising antibacterial properties.

Novel compounds of the deoxyactagardine A and B type have now been identified with optimised properties, making them particularly suitable for the use in the treatment of microbial infections, for example *Clostridium* infection, such as *C. perfringens, C. difficile, C. tetani*, and/or *C. botulinum*, in particular *C. difficile*, especially infection of the colon and/or lower intestines and diarrhea associated with the microbial infection.

In one aspect there is provided a compound of formula (I)

(I)

wherein
A is —$C_{1-4}$ alkyl;
B is —$C_{1-4}$ alkyl;
X is —NH(CH$_2$)$_p$NH$_2$;
p is an integer 2 to 12;
Z is —NR$^1$R$^2$;
R$^1$ is H or $C_{1-4}$ alkyl,
R$^2$ is H, an amino acid or $C_{1-4}$ alkyl, and
pharmaceutically acceptable salts, hydrates and solvates thereof.

The compounds of the disclosure are advantageous because they have very high antibacterial activity against one or more strains of *C. difficile*, for example when activity is measured by a standard test such as minimum inhibitory concentrations (MICs), generally the compounds of the disclosure have an MIC of 2 μg/ml or lower against one or more *C. difficile* strains. Furthermore, certain compounds of the disclosure have very high activity against a number of common strains of *C. difficile*.

Additionally, the compounds of the present disclosure are particularly suited to administration to humans and animals because they have low antibacterial activity against the naturally occurring healthy intestinal flora found in the body. In the case of treatment of diarrhea induced by a microbial infection such as *C. difficile* it is expected that a reduced recurrence of symptoms will be observed after treatment with the present compounds in comparison to treatment with known antibiotics because of the ability of the natural flora to survive the treatment with the present compounds. In particular the compounds of the disclosure show very low activity against *Bacteroides fragilis, Bacteroides thetaiotaomicron, Bifidobacterium longum, Lactobacillus rhamnosus*, and moderately low activity against *Peptostreptococcus anaerobius* and *Bifidobacterium adolescentis*.

What is more, when delivered orally the compounds of the disclosure are not absorbed systemically, which allows a relatively high concentration of the active to be delivered to the target in the colon/intestines. Thus because there is no systemic delivery of the compounds when administered orally, then this may minimise any potential exposure to side effects for patients.

*C. difficile* infection and/or overgrowth is a common problem for patients during hospitalisation. It presents a real burden to the health care system and may be life threatening to vulnerable patients such as elderly patients.

At the present time vancomycin is the standard treatment for serious cases of *C. difficile* infection. Therefore, whilst alternative compounds for use in the treatment of *C. difficile* would be useful, such compounds are required to have an activity approximately equal to or better than that of vancomycin.

Certain compounds are under investigation for the treatment of *C. difficile* and/or vancomycin resistant enterococci but often the active ingredient is degraded by the acid and/or enzymes in the stomach or intestines. Such compounds require parenteral delivery or special formulations such as enteric coating or capsule formulations to ensure that the active ingredient is delivered to the colon in an undegradated form. Surprisingly, the present compounds, although comprising peptide components, are not degraded to any significant extent by stomach acid or enzymes. Thus the compounds of the disclosure are particularly suitable for oral delivery. This can be advantageous in that it allows the flexibility to formulate the compounds in a simple and effective formulation enabling delivery of an undegraded active locally to the colon.

Certain compounds of the present disclosure, can be prepared by synthesising deoxyactagardine B as an intermediate in *A. liguriae*. The yield of deoxyactagardine B is double or more the yield of actagardine A type intermediates prepared by *Actinoplanes garbadinensis*. This can be important from a commercial/processing perspective.

The physical properties of the compounds of the disclosure such as solubility, stability and the like are adquate for the intended therapeutic use.

DETAILED DESCRIPTION

Alkyl in the context of the present disclosure refers to straight chain or branched chain alkyl, for example methyl, ethyl, propyl, isopropyl, n-butyl or t-butyl.

In one embodiment A has a structure corresponding to an alkyl side chain of a natural amino acid containing up to 4 carbons.

In one embodiment A is —$CH_3$.

In one embodiment A is a branched chain alkyl, for example —$CH(CH_3)_2$, —$CH_2CH(CH_3)_2$, or —$CH(CH_3)CH_2CH_3$ such as —$CH(CH_3)_2$ or —$CH_2CH(CH_3)_2$, particularly —$CH_2CH(CH_3)_2$.

In one embodiment B has a structure corresponding to an alkyl side chain of a natural amino acid containing up to 4 carbons.

In one embodiment B is —$CH_3$.

In one embodiment B is a branched chain alkyl, for example —$CH(CH_3)_2$, —$CH_2CH(CH_3)_2$, or —$CH(CH_3)CH_2CH_3$, such as —$CH(CH_3)_2$ or —$CH_2CH(CH_3)_2$ or such as —$CH(CH_3)_2$ or —$CH_2CH(CH_3)_2$, particularly —$CH(CH_3)_2$.

In one aspect A is —$CH_2CH(CH_3)_2$ and B is —$CH(CH_3)_2$.

In one embodiment $R^1$ is H.

In one embodiment $R^2$ is H.

In one embodiment $R^2$ is the L or D isomer form of an amino acid residue. In one embodiment $R^2$ is the L or D isomer form of —$C(O)CH(CH_3)NH_2$.

In one embodiment $R^2$ is an amino acid residue selected from alanine, cysteine, aspartic acid, glutamic acid, phenylalanine, glycine, histidine, isoleucine, lysine, leucine, methionine, asparagine, proline, glutamine, arginine, serine, threonine, valine, tryptophan and tyrosine.

In one embodiment $R^2$ is an amino acid residue selected from phenylalanine, tyrosine and alanine (i.e. —$C(O)CH(CH_3)NH_2$).

In one embodiment Z is —$NH_2$.

In one aspect A is —$CH_2CH(CH_3)_2$ and B is —$CH(CH_3)_2$ and Z is —$NH_2$.

In one embodiment p is 2, 3, 4, 5, 6, 7, 8, 9, 10, 11 or 12, such as 2, 3, 7, 9 or 12, in particular 7, 9 or 12. In one embodiment p is 7. In another embodiment p is 9 or 12.

In one embodiment p is 3 to 12 or 3 to 8.

Each and every compatible combination of the embodiments described above is explicitly disclosed herein, as if each and every combination was individually and explicitly recited.

In one aspect the disclosure provides a compound of formula (II):

(II)

or a pharmaceutically acceptable salt, hydrate or solvate thereof.

Compounds of the disclosure have an MIC against at least one strain of *C. difficile* of 1 µg/ml or less and generally an activity against other common strains of *C. difficile* of 2 µg/ml or less.

Some compounds of the disclosure, for example the compound of formula II, have activity of 1 µg/ml or less against many common strains of *C. difficile*.

Methods of preparing compounds similar to compounds of the present disclosure are described in WO 2007/083112.

The compounds of the present disclosure may be in the form of and/or may be administered as a pharmaceutically acceptable salt. For a review on suitable salts see Berge et al., J. Pharm. Sci, 1977, 66, 1-19.

Typically, a pharmaceutically acceptable salt may be readily prepared by using a desired acid or base as appropriate. The salt may precipitated from solution and be collected by filtration or may be recovered by evaporation of the solvent, for example, a compound of formula (I) may be dissolved in a suitable solvent, for example an alcohol such as methanol, and the acid may be added in the same solvent or another suitable solvent. The resulting acid addition salt may then be precipitated directly, or by addition of a less polar solvent such as diisopropyl ether or hexane, and isolated by filtration.

The skilled person will appreciate that where the compound of formula (I) or (II) contains more than one basic group bis salts or tris salts may also be formed and are salts according to the present disclosure.

Suitable addition salts are formed from inorganic or organic acids which form non-toxic salts and examples are lactobionate, mandelate (including (S)-(+)-mandelate, (R)-(−)-mandelate and (R,S)-mandelate), hydrochloride, hydrobromide, hydroiodide, sulfate, bisulfate, nitrate, phosphate, hydrogen phosphate, glutamate, acetate, trifluoroacetate, maleate, malate, fumarate, lactate, tartrate, citrate, formate, gluconate, succinate, ethyl succinate (4-ethoxy-4-oxo-butanoate), pyruvate, oxalate, oxaloacetate, saccharate, benzoate, glucolate, glucurinate, alkyl or aryl sulphonates (eg methanesulphonate, ethanesulphonate, benzenesulphonate or p-toluenesulphonate) and isethionate. An additional or alternative example is mesylate.

Pharmaceutically acceptable base salts include ammonium salts, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compounds of formula (I) or (II) are within the scope of the disclosure. The salts of the compound of formula (I) or (II) may form solvates (e.g. hydrates) and the disclosure also includes all such solvates. The term "prodrug" as used herein means a compound which is converted within the body, e.g. by hydrolysis in the blood, into its active form that has medical effects. Pharmaceutically acceptable prodrugs are described in T. Higuchi and V. Stella, "Prodrugs as Novel Delivery Systems", Vol. 14 of the A.C.S. Symposium Series; Edward B. Roche, ed., "Bioreversible Carriers in Drug Design", American Pharmaceutical Association and Pergamon Press, 1987; and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release a compound of formula (I) or (II) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this disclosure wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of formula (I) or (II). Further, in the case of a carboxylic acid (—COOH), esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

References hereinafter to a compound according to the disclosure include both compounds of formula (I) or (II) and their pharmaceutically acceptable salts and derivatives.

With regard to stereoisomers, the compounds of formula (I) or (II) have more than one asymmetric carbon atom. In the general formula (I) or (II) as drawn, the solid wedge shaped bond indicates that the bond is above the plane of the paper. The broken bond indicates that the bond is below the plane of the paper.

It will be appreciated that the substituents in compounds of formulae (I) or (II) may also have one or more asymmetric carbon atoms.

The compounds of structure (I) or (II) may occur as individual enantiomers or diastereomers. All such isomeric forms are included within the present invention, including mixtures thereof.

Separation of diastereoisomers or cis and trans isomers may be achieved by conventional techniques, e.g. by fractional crystallisation, chromatography or HPLC. A stereoisomeric mixture of the agent may also be prepared from a corresponding optically pure intermediate or by resolution, such as by HPLC, of the corresponding mixture using a suitable chiral support or by fractional crystallisation of the diastereoisomeric salts formed by reaction of the corresponding mixture with a suitable optically active acid or base, as appropriate. Compounds of formula (I) or (II) as described herein also extend to tautomeric forms thereof, for example, keto/enol tautomers.

The compounds of formula (I) or (II) may be in crystalline or amorphous form. Furthermore, some of the crystalline forms of the compounds of structure (I) or (II) may exist as polymorphs, all forms which are included in the present disclosure.

In another aspect, the invention provides a pharmaceutical composition comprising, as active ingredient, a compound of the invention or a pharmaceutically acceptable derivative thereof in association with a pharmaceutically acceptable excipient, diluent and/or carrier for use in therapy, and in particular, in the treatment of human or animal subjects suffering from a condition susceptible to amelioration by an antimicrobial compound.

In another aspect, the invention provides a pharmaceutical composition comprising a therapeutically effective amount of the compounds of the present disclosure and a pharmaceutically acceptable excipient, diluent and/or carrier (including combinations thereof).

There is further provided by the present disclosure a process of preparing a pharmaceutical composition, which process comprises mixing a compound of the invention or a pharmaceutically acceptable derivative thereof, together with a pharmaceutically acceptable excipient, diluent and/or carrier.

The compounds of the invention may be formulated for administration in any convenient way for use in human or veterinary medicine and the disclosure therefore includes within its scope pharmaceutical compositions comprising a compound of the invention adapted for use in human or veterinary medicine. Such compositions may be presented for use in a conventional manner with the aid of one or more suitable excipients, diluents and/or carriers. Acceptable excipients, diluents and carriers for therapeutic use are well known in the pharmaceutical art, and are described, for example, in Remington's Pharmaceutical Sciences, Mack Publishing Co. (A. R. Gennaro edit. 1985). The choice of pharmaceutical excipient, diluent and/or carrier can be selected with regard to the intended route of administration and standard pharmaceutical practice. The pharmaceutical compositions may comprise as—or in addition to—the excipient, diluent and/or carrier any suitable binder(s), lubricant(s), suspending agent(s), coating agent(s), solubilising agent(s).

Preservatives, stabilisers, dyes and even flavouring agents may be provided in the pharmaceutical composition. Examples of preservatives include sodium benzoate, sorbic acid and esters of p-hydroxybenzoic acid. Antioxidants and suspending agents may be also used.

For some embodiments, the agents of the present disclosure may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO 91/11172, WO 94/02518 and WO 98/55148.

The compounds of the disclosure may be milled using known milling procedures such as wet milling to obtain a particle size appropriate for tablet formation and for other formulation types. Finely divided (nanoparticulate) preparations of the compounds of the invention may be prepared by processes known in the art, for example see International Patent Application No. WO 02/00196 (SmithKline Beecham).

The routes for administration (delivery) include, but are not limited to, one or more of: oral (e.g. as a dry powder/free flowing particulate formulation, tablet, capsule, or as an ingestable solution or suspension) rectal, buccal, and sublingual. The compounds of the disclosure are particularly useful for oral delivery.

In some instances it may be possible to deliver the compounds of the disclosure by a topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), or transdermal route.

There may be different composition/formulation requirements depending on the different delivery systems. By way of example, the pharmaceutical composition of the present disclosure may be formulated to be delivered using a mini-pump or by a mucosal route, for example, as a nasal spray or aerosol for inhalation or ingestable solution, or parenterally in which the composition is formulated by an injectable form, for delivery by, for example, an intravenous, intramuscular or subcutaneous route. Alternatively, the formulation may be designed to be delivered by both routes.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner. It is to be understood that not all of the compounds need be administered by the same route. Likewise, if the composition comprises more than one active component, then those components may be administered by different routes.

The compositions of the disclosure include those in a form especially formulated for parenteral, oral, buccal, rectal, topical, implant, ophthalmic, nasal or genito-urinary use. In one aspect of the invention, the agents are delivered orally, hence, the agent is in a form that is suitable for oral delivery.

If a compound of the present disclosure is administered parenterally, then examples of such administration include one or more of: intravenously, intraarterially, intraperitoneally, intrathecally, intraventricularly, intraurethrally, intrasternally, intracranially, intramuscularly or subcutaneously administering the agent, and/or by using infusion techniques.

The compounds of the invention can be administered (e.g. orally or topically) in the form of tablets, capsules, ovules, elixirs, solutions or suspensions, which may contain flavouring or colouring agents, for immediate-, delayed-, modified-, sustained-, pulsed- or controlled-release applications.

The compounds of the invention may also be presented for human or veterinary use in a form suitable for oral or buccal administration, for example in the form of solutions, gels, syrups, mouth washes or suspensions, or a dry powder for constitution with water or other suitable vehicle before use, optionally with flavouring and colouring agents. Solid compositions such as tablets, capsules, lozenges, pastilles, pills, boluses, powder, pastes, granules, bullets or premix preparations may also be used. Solid and liquid compositions for oral use may be prepared according to methods well known in the art. Such compositions may also contain one or more pharmaceutically acceptable carriers and excipients which may be in solid or liquid form.

The tablets may contain excipients such as microcrystalline cellulose, lactose, sodium citrate, calcium carbonate, calcium sulphate, dibasic calcium phosphate and glycine, mannitol, pregelatinised starch, corn starch, potato starch, disintegrants such as sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia.

Additionally, lubricating agents such as magnesium stearate, stearic acid, glyceryl behenate and talc may be included.

Solid compositions of a similar type may also be employed as fillers in gelatin or HPMC (hydroxypropyl methylcellulose) capsules. Preferred excipients in this regard include microcrystalline cellulose, lactose, calcium carbonate, calcium sulphate, dibasic calcium phosphate and, mannitol, pregelatinised starch, corn starch, potato starch or high molecular weight polyethylene glycols. For aqueous suspensions and/or elixirs, the agent may be combined with various sweetening or flavouring agents, colouring matter or dyes, with emulsifying and/or suspending agents and with diluents such as water, ethanol, propylene glycol and glycerin, and combinations thereof.

Capsules, may be filled with a powder (of medicament alone or as blend with selected filler(s)) or alternatively a liquid, each comprising one or more compounds of formula (I) or (II) and a carrier. Where the capsule is filled with a powder the compounds of formula (I) or (II) and/or the carrier may be milled or micronised to provide material with an appropriate particle size.

Compounds of the disclosure may be coated, for example with as an enteric coating when administered orally as a tablet or capsule. The tablet or capsule, as appropriate, may, for example be coated by a thin film such as a EUDRAGIT® film available from Rohm Pharma Polymers, which allows controlled dissolution in the gastrointestinal tract. The films are available as cationic polymers such as EUDRAGIT® E 100 (aminoalkyl methacylate copolymers) or as anionic acrylic polymers such as EUDRAGIT® L (methacrylic acid copolymers) and EUDRAGIT S.

Permeable acrylic polymers such as EUDRAGIT® RL (amino methacrylate copolymer) and EUDRAGIT® RS are also available.

These coating formulations may be prepared as an aqueous dispersion including optional ingredients such as talc, silicone antifoam emulsion, polyethylene glycol. Alternatively the coating formulation may be prepared as an organic polymer solution.

Alternatively, tablets may be coated using OPADRY® (Surelease®) coating systems, available from Colorcon. Aqueous systems generally comprise up to 15% w/w of OPADRY®. Organic solvent systems generally comprise up to 5% w/w of OPADRY®. The coatings may be prepared by known techniques, for example by;

1. weighing the required quantity of OPADRY® film coating system,
2. weighing the required quantity of water or other solvent(s) into a mixing vessel,
3. with a mixing propeller in the centre of the vessel and as close to the bottom of the vessel as possible, stirring the solvents to form a vortex without drawing air into the liquid,
4. steadily and quickly adding the OPADRY® powder to the vortex, avoiding powder flotation on the liquid surface,
5. increasing the stirrer speed in order to maintain the vortex, if required, and
6. after all the powder ingredients have been added, reducing the mixer speed and continuing mixing for approximately 45 minutes.

Coatings can be applied by known techniques, using tablet coating machines.

The thickness of the coating applied is generally in the range 5 to 35 microns such as 10 to 30 microns, more specifically 10 or 20 microns, depending on the required effect. Alternatively, the tablet or a capsule, as appropriate, may be filled into another capsule (preferably a HPMC capsule such as Capsugel®) to provide either a tablet in capsule or capsule in capsule configuration, which when administered to a patient yields controlled dissolution in the gastrointestinal tract thereby providing a similar effect to an enteric coating. Thus in one aspect the disclosure provides a solid dose formulation of a compound of formula (I) or (II) for example where the formulation has an enteric coating.

In another aspect the disclosure provides a solid dose formulation comprising a protective capsule as outer layer, for example as a tablet in a capsule or a capsule in a capsule. The enteric coating may provide an improved stability profile over uncoated formulations. The compounds of the disclosure may also be administered orally in veterinary medicine in the form of a liquid drench such as a solution, suspension or dispersion of the active ingredient together with a pharmaceutically acceptable carrier or excipient.

The compounds of the invention may also, for example, be formulated as suppositories e.g. containing conventional suppository bases for use in human or veterinary medicine or as pessaries e.g. containing conventional pessary bases.

The compounds of the disclosure may also be used in combination with other therapeutic agents. The disclosure thus provides, in a further aspect, a combination comprising a compound of formula (I) or (II) or a pharmaceutically acceptable derivative thereof together with a further therapeutic agent. The combination may, for example be a combination of a compound of formula (I) or (II) and an antibiotic, such as vancomycin. The combination may be provided as a co-formulation or simply packaged together as separate formulations, for simultaneous or sequential delivery.

When a compound of the disclosure or a pharmaceutically acceptable derivative thereof is used in combination with a second therapeutic agent active against the same disease state the dose of each compound may differ from that when the compound is used alone. Appropriate doses will be readily appreciated by those skilled in the art. It will be appreciated that the amount of a compound of the disclosure required for use in treatment will vary with the nature of the condition being treated and the age and the condition of the patient and will be ultimately at the discretion of the attendant physician or veterinarian. The compounds of the present disclosure may for example be used for administration with other active ingredients such as corticosteroids, as appropriate.

The combinations referred to above may conveniently be presented for use in the form of a pharmaceutical formulation and thus pharmaceutical formulations comprising a combination as defined above together with a pharmaceutically acceptable carrier or excipient comprise a further aspect of the disclosure. The individual components of such combinations may be administered either sequentially or simultaneously in separate or combined pharmaceutical formulations by any convenient route.

When administration is sequential, either the compound of the disclosure or the second therapeutic agent may be administered first. When administration is simultaneous, the combination may be administered either in the same or different pharmaceutical composition.

When combined in the same formulation it will be appreciated that the two compounds must be stable and compatible with each other and the other components of the formulation. When formulated separately they may be provided in any convenient formulation, conveniently in such manner as are known for such compounds in the art.

The compositions may contain from 0.01-99% of the active material. For topical administration, for example, the composition will generally contain from 0.01-10%, more preferably 0.01-1% of the active material.

Typically, a physician will determine the actual dosage which will be most suitable for an individual subject. The specific dose level and frequency of dosage for any particular individual may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

For oral and parenteral administration to humans, the daily dosage level of the agent may be in single or divided doses. For systemic administration the daily dose as employed for adult human treatment will range from 2-100 mg/kg body weight, preferably 5-60 mg/kg body weight, which may be administered in 1 to 4 daily doses, for example, depending on the route of administration and the condition of the patient. When the composition comprises dosage units, each unit will preferably contain 100 mg to 1 g of active ingredient. The duration of treatment will be dictated by the rate of response rather than by arbitrary numbers of days. In one embodiment the treatment regime is continued for 1, 2, 3, 4, 5, 6, 7, 8, 9, 10, 11, 12, 13, 14, 15, 16, 17, 18, 19, 20, 21 or more days.

In one aspect, the disclosure provides use of a compound of formula (I) or (II) in therapy, for example, for treatment of microbial infections such as *C. difficile* infection, in particular diarrhea associated therewith, or one or more microbial infections described herein, particularly by oral delivery of a compound of formula (I) or (II).

In one aspect there is provided use of a compound of formula (I) or (II) for the treatment of cecitis (in an animal subject).

In one aspect the compound of formula (I) or (II) are employed for controlling bacterial overgrowth syndrome. Overgrowth syndrome (BOS) occurs when the normally low bacterial colonization in the upper GI tract and/or lower intestines significantly increases.

In one aspect there is provided use of a compound of formula (I) or (II) for the prophylaxis, treatment or maintenance of IBS (irritable bowel syndrome). For an example of the use of antibiotics in the treatment of IBS, see Rifaximin Treatment for Symptoms of Irritable Bowel Syndrome. Andrea L. Fumi and Katherine Trexler, *The Annals of Pharmacotherap,* 2008, 4, 408.

In one embodiment a compound of formula (I) or (II) is useful in the treatment of ulcerative colitis including prophylactic treatment to prevent recurrence thereof. The compounds may be particularly suitable for the treatment of steroid refractory ulcerative colitis. See for example Steroid-refractory ulcerative colitis treated with corticosteroids, metronidazole and vancomycin: a case report J. Miner, M. M Gillan, P. Alex, M Centola, *BMC Gastroenterology* 2005, 5:3.

The compounds of the present disclosure may be particularly useful for long term treatment.

As described above the compounds of the present disclosure may be employed in the treatment of humans and/or animals.

In one aspect there is provided a compound of formula (I) or (II) for the manufacture of a medicament for the for treatment of microbial infections such as *C. difficile* infection, in particular diarrhea associated therewith.

In one aspect there is provided a method of treatment comprising the step of administering a therapeutically effective amount of a compound of formula (I) or (II) or a pharmaceutical composition containing the same to a patient (human or animal) in need thereof, for example for the treatment of an infection/illness or disease as described herein.

In the context of this specification "comprising" is to be interpreted as "including".

Aspects of the invention comprising certain elements are also intended to extend to alternative embodiments "consisting" or "consisting essentially" of the relevant elements.

EXAMPLES

Example 1

Deoxyactagardine B (7-amino-1-heptylamide monocarboxamide)

Figure 4:
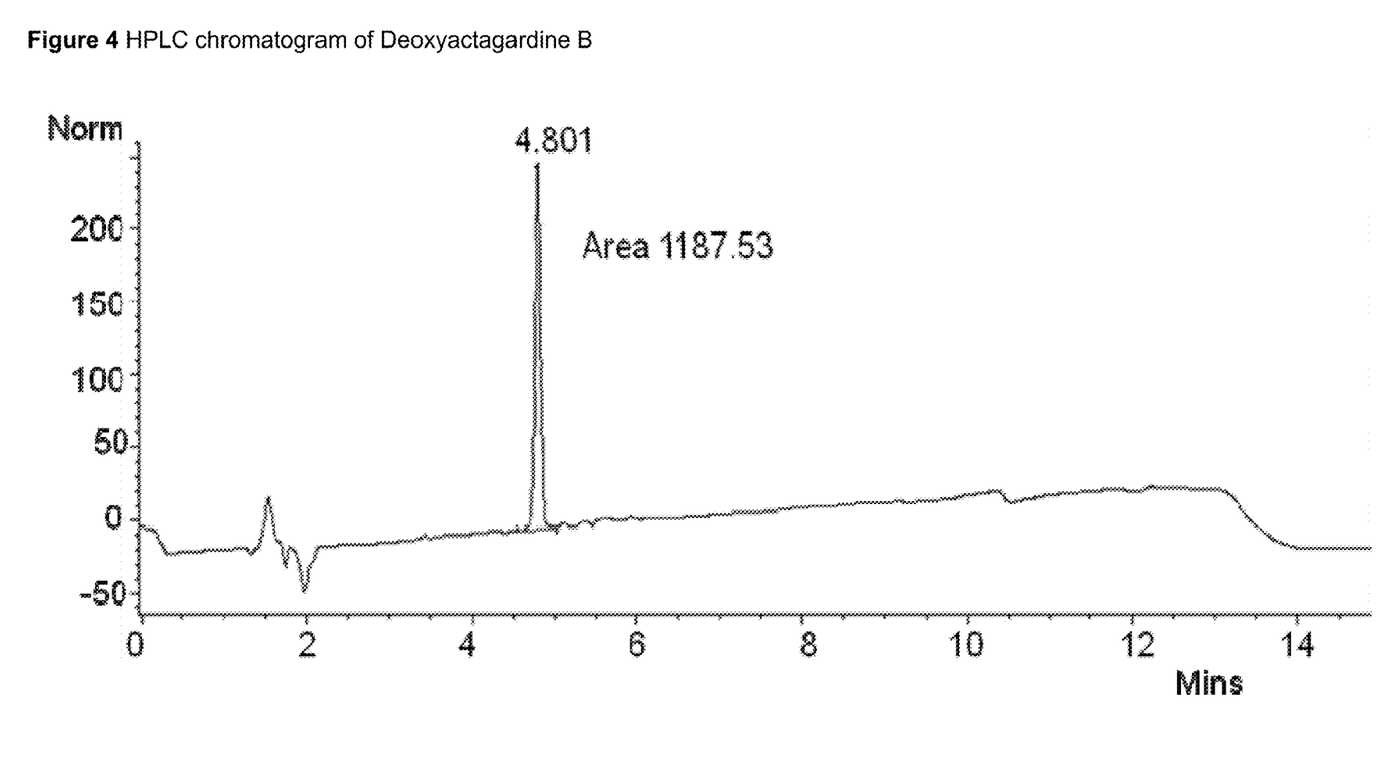
FIG. 4 shows a HPLC analysis of the starting materials for Example 1.
Figure 5:
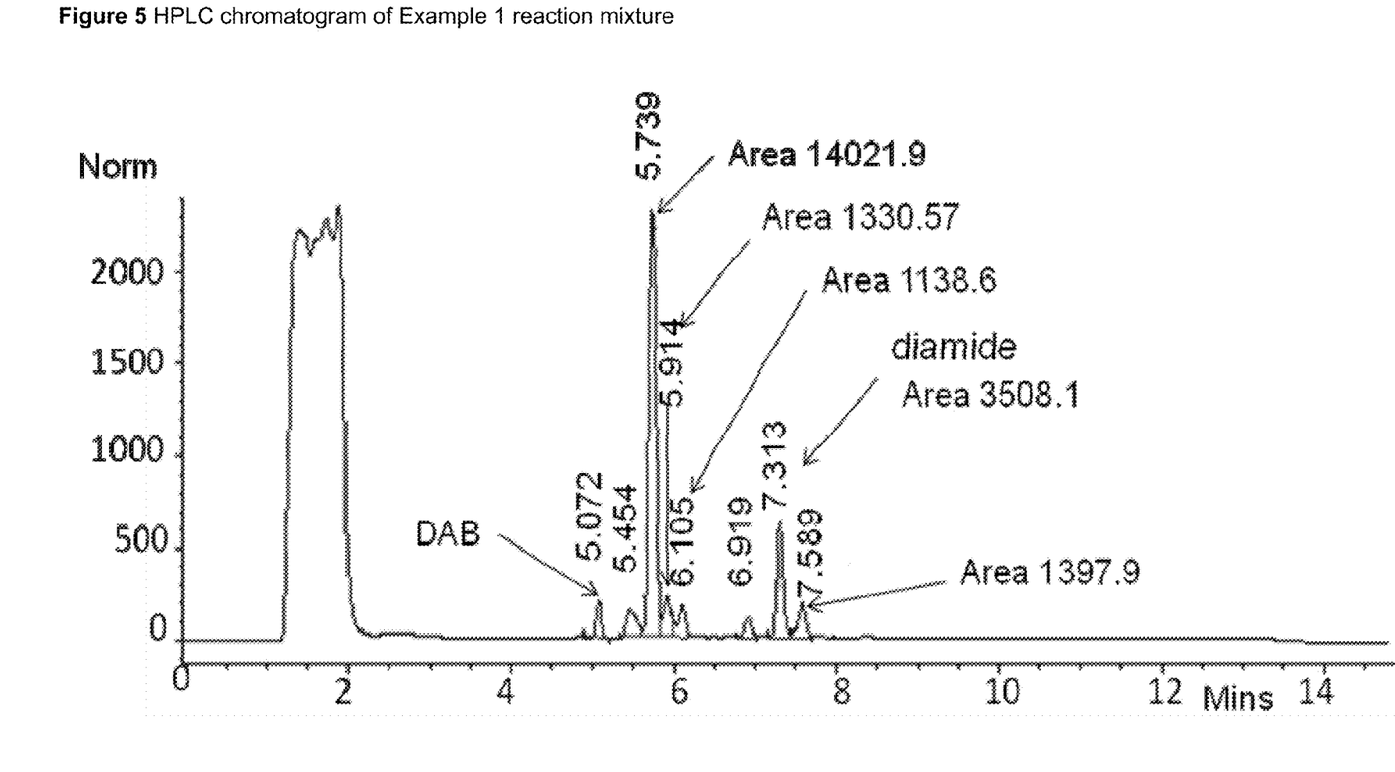
FIG. 5 shows a HPLC analysis after the reaction for Example 1 has been completed.

Deoxyactagardine B (2.5 g), 1,7-diaminoheptane (0.52 g) and diisopropylethylamine (0.44 ml) were dissolved in dry dimethylformamide (10 ml). A solution of benzotriazole-1-yl-oxy-tris-pyrrolidino-phosphonium hexafluorophosphate (PyBOP) (1.04 g) in dry dimethylformamide (5 ml) was added portionwise over 2 h. The reaction was followed by analytical HPLC (See Table 1) and PyBOP was added until the starting material had been consumed (FIGS. 4 and 5).

TABLE 1

Analytical HPLC conditions for the separation of lantibiotic (e.g. actagardine, actagardine B, or deoxy-actagardine B) and diaminoalkane derivatised products.

| Column: | Zorbax 5μ C18(2) 150 × 4.6 mm | | |
|---|---|---|---|
| Mobile Phase A: | 30% Acetonitrile in 20 mM potassium phosphate buffer pH 7.0 | | |
| Mobile Phase B: | 65% Acetonitrile in 20 mM potassium phosphate buffer pH 7.0 | | |
| Flow rate: | 1 ml/min | | |
| Gradient: | Time 0 min | 100% A | 0% B |
| | Time 10 min | 0% A | 100% B |
| | Time 11 min | 0% A | 100% B |
| | Time 11.2 min | 100% A | 0% B |
| Cycle time 15 min | | | |
| Injection volume: | 10 μl | | |
| Detection: | 210 nm | | |

Figure 6:
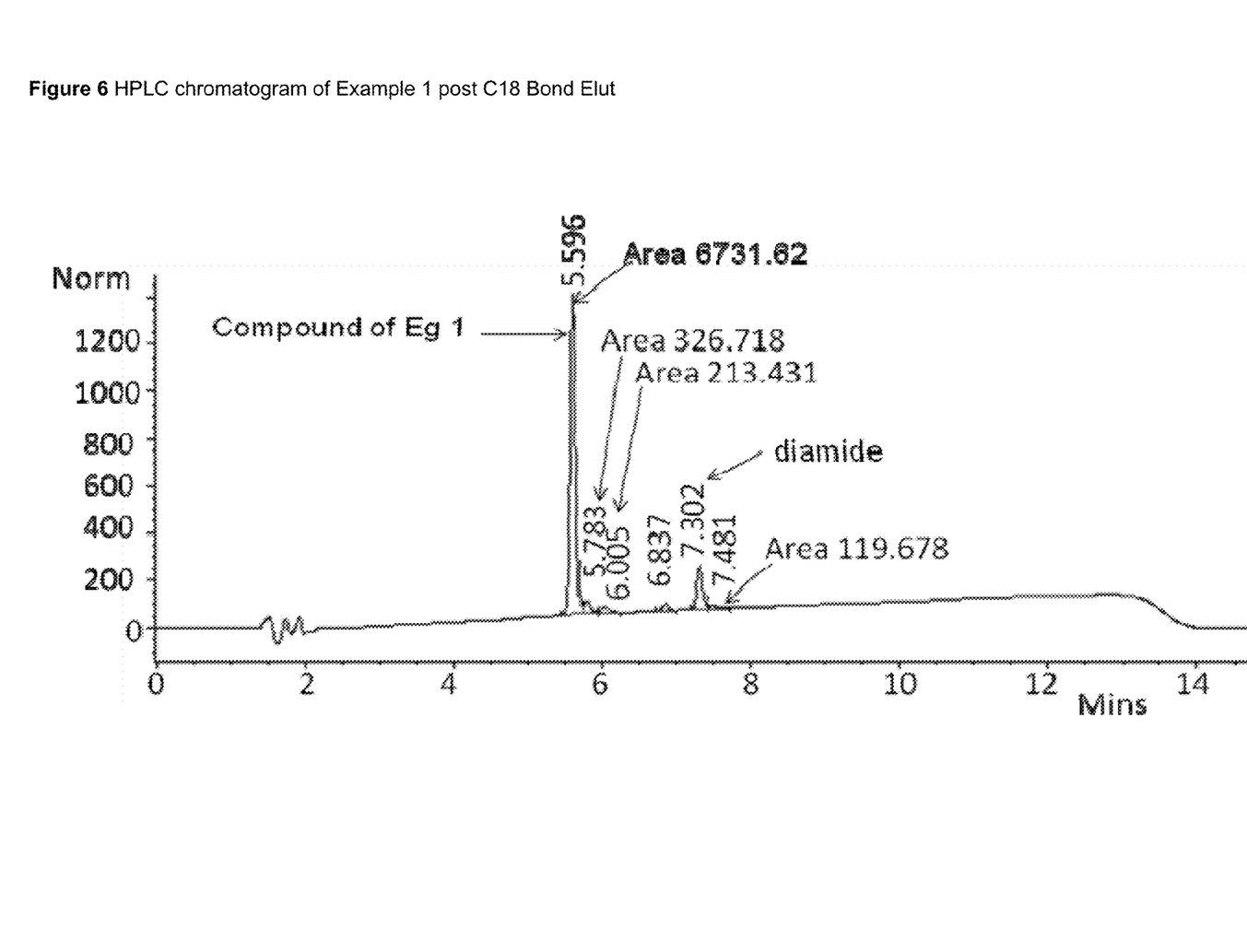
FIG. 6 shows a HPLC analysis after C18 Bond Elut concentration of the compound of Example 1.
Figure 7:
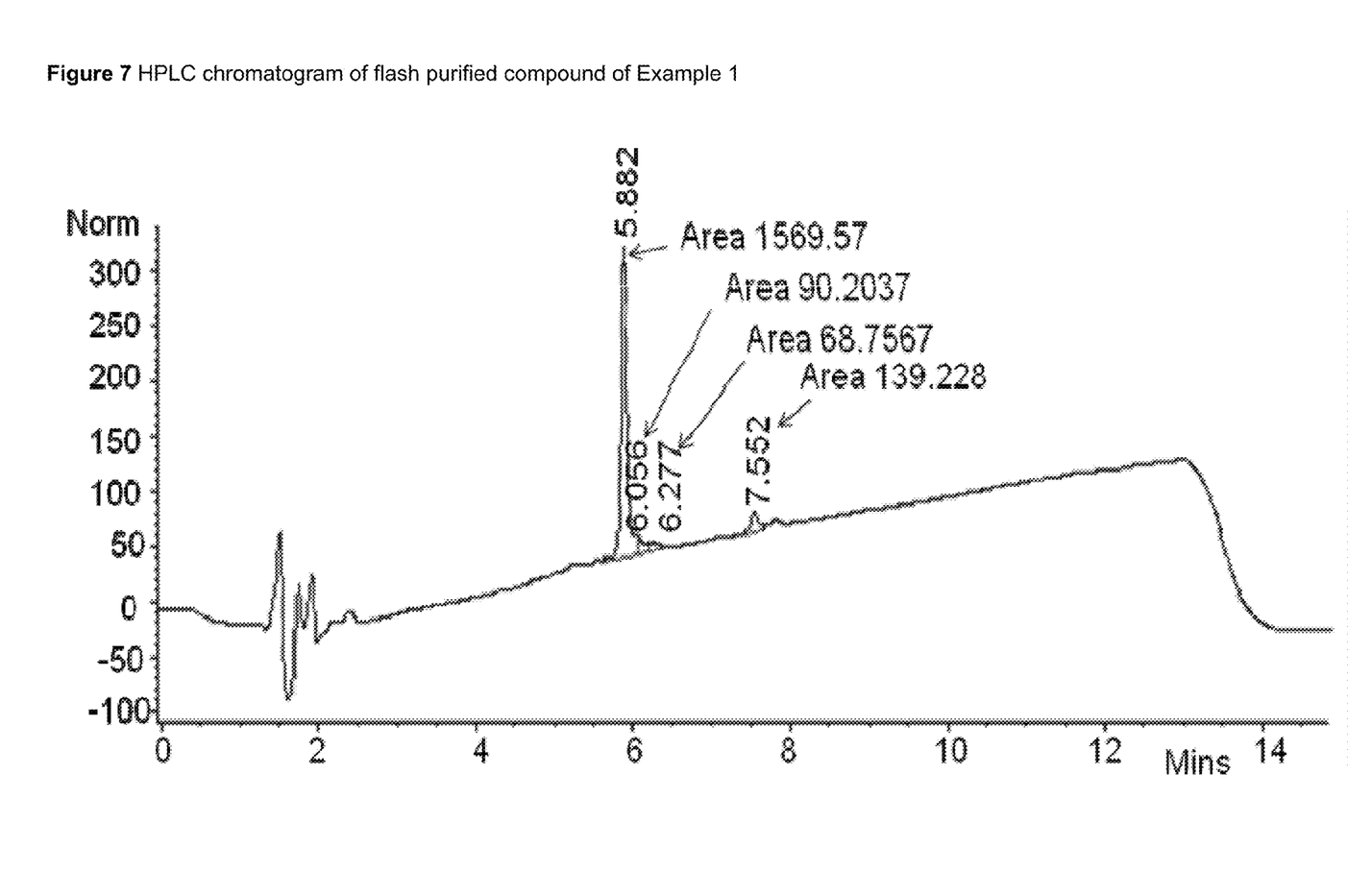
FIG. 7 shows a HPLC analysis of the compound of Example 1 after flash chromatography.

The crude reaction mixture was poured into 30% aqueous methanol and the resulting solution was loaded on to a Varian Bond Elut C18 column (30 g). The column was then washed sequentially with 50%, 60%, 70%, 80%, 90% aqueous methanol, with most of the desired material eluting in the 70% fraction (FIG. 6) Column chromatography on silica gel (eluent dichloromethane:ethanol:ammonia 10:8:1) gave material of >90% purity by U.V. at 210 nm (FIG. 7). Yield 1.4 g. Mass calc $(M+2H)^{+2}$ 993, found 992.91.

The product was analysed by $^{13}C$ NMR spectroscopy at 500 MHz (solvent $D_3$ acetonitrile:water in a ratio 7:3). A peak listing is provided in Table 2.

TABLE 2

Carbon 13 peak listing for Example 1.

| PEAK | [ppm] |
|---|---|
| 1 | 181.3149 |
| 2 | 175.3919 |
| 3 | 174.8404 |
| 4 | 174.6462 |
| 5 | 174.3911 |
| 6 | 174.2256 |
| 7 | 174.0976 |
| 8 | 173.8498 |
| 9 | 173.4321 |
| 10 | 173.3003 |
| 11 | 173.1919 |
| 12 | 172.8374 |
| 13 | 172.5363 |
| 14 | 172.5226 |
| 15 | 171.6244 |
| 16 | 171.403 |
| 17 | 171.2443 |
| 18 | 171.2186 |
| 19 | 137.4317 |
| 20 | 128.2591 |
| 21 | 125.4133 |
| 22 | 122.6186 |
| 23 | 120.101 |
| 24 | 119.489 |
| 25 | 119.2236 |
| 26 | 112.6147 |
| 27 | 110.3448 |
| 28 | 62.6628 |
| 29 | 62.3103 |
| 30 | 61.9417 |
| 31 | 60.0459 |
| 32 | 59.2589 |
| 33 | 57.6883 |
| 34 | 57.5602 |
| 35 | 57.1782 |
| 36 | 56.3394 |
| 37 | 55.779 |
| 38 | 55.1894 |
| 39 | 54.8993 |
| 40 | 54.8157 |
| 41 | 54.4243 |
| 42 | 53.0651 |
| 43 | 52.6472 |
| 44 | 51.5046 |
| 45 | 47.0088 |
| 46 | 44.8668 |
| 47 | 44.6775 |
| 48 | 44.5744 |
| 49 | 43.8023 |
| 50 | 42.6752 |
| 51 | 41.1394 |
| 52 | 40.7135 |
| 53 | 40.0986 |
| 54 | 36.7443 |
| 55 | 36.5221 |
| 56 | 36.0111 |
| 57 | 35.0293 |
| 58 | 33.5143 |
| 59 | 31.0095 |
| 60 | 30.9257 |
| 61 | 30.2204 |
| 62 | 29.4444 |
| 63 | 28.9958 |
| 64 | 28.1579 |
| 65 | 27.8264 |
| 66 | 27.3108 |
| 67 | 26.8943 |
| 68 | 26.6716 |

TABLE 2-continued

Carbon 13 peak listing for Example 1.

| PEAK | [ppm] |
|---|---|
| 69 | 26.0067 |
| 70 | 25.6053 |
| 71 | 25.5072 |
| 72 | 23.0708 |
| 73 | 22.7664 |
| 74 | 22.7369 |
| 75 | 21.9216 |
| 76 | 20.7945 |
| 77 | 20.7139 |
| 78 | 20.5133 |
| 79 | 19.7487 |
| 80 | 19.6807 |
| 81 | 19.3537 |
| 82 | 18.6924 |
| 83 | 17.3511 |
| 84 | 16.1335 |
| 85 | 12.0709 |
| 86 | 1.8865 |
| 87 | 1.7212 |
| 88 | 1.5557 |
| 89 | 1.3899 |
| 90 | 1.2242 |
| 91 | 1.0588 |
| 92 | 0.8934 |

Example 2

Preparation of the Methanesulfonate Salt of the Compound of Example 1

For the purpose of obtaining solutions suitable for oral or intravenous dosing, the methanesulfonate salt of the compound of Example 1 was found to be suitable.

The compound of Example 1 was suspended in water and an excess of methanesulfonic acid was added to give a clear solution. Excess methanesulfonic acid was removed by loading the solution onto a Bond Elut C18 column that had been conditioned according to the manufacturers instructions, washing the column thoroughly with water and eluting the methanesulfonate salt with methanol. The solvent was removed by evaporation leaving the methanesulfonate salt as a white powder.

The methanesulfonate salt of the compound of Example 1 was soluble at approximately 20 mg/ml in water.

Example 3

Alternative Route for Preparation of Compound of Example 1

Deoxyactagardine B [7-(t-butoxycarbonylamido)-1-heptylamide monocarboxamide]

Was prepared employing the process described for compound Example 1 from Deoxyactagardine B and 7-(t-butoxycarbonylamido)-1-aminoheptane. 75% $(M+2H)^{+2}$ 1043, found 1044.11. The t-butoxycarbonate was hydrolysed by treatment with 4N aqueous hydrochloric acid for 3 h at room temperature. The mixture was neutralised to pH7 and purification was carried out as described for Example 1 to provide the title compound.

Yield 65%.

The compounds below were prepared by analogous methods to that employed for Example 1.

Example 4

Deoxyactagardine B (2-amino-1-ethylamide monocarboxamide)

Was prepared from deoxyactagardine and 1,2-ethylenediamine employing the process described above for Example 1.
Yield 96%. Mass calc $(M+2H)^{+2}$ 958, found 959.02

Example 5

Deoxyactagardine B (3-amino-1-propylamide monocarboxamide)

Was prepared from deoxyactagardine and 1,3-diaminopropane employing the process described above for Example 1.
Yield 87%. Mass calc $(M+2H)^{+2}$ 965, found 965.04

Example 6

Deoxyactagardine B (5-amino-1-pentylamide monocarboxamide)

Was prepared from deoxyactagardine and 1,5-diaminopentane employing the process described above for Example 1.
Yield 83%. Mass calc $(M+2H)^{+2}$ 979, found 980.06

Example 7

Deoxyactagardine B (9-amino-1-nonylamide monocarboxamide)

Was prepared from deoxyactagardine and 1,9-diaminononane employing the process described above for Example 1.
Yield 84%. Mass calc $(M+2H)^{+2}$ 1007, found 1007.51

Example 8

Deoxyactagardine B (12-amino-1-dodecylamide monocarboxamide)

Was prepared from deoxyactagardine and 1,12-diaminododecane employing the process described above for Example 1.
Yield 74%. Mass calc $(M+2H)^{+2}$ 1028, found 1027.51

Example 9

Antibacterial Activity of Type-B Lantibiotics

The compounds of the invention show antimicrobial activity in vitro and in vivo. They are active against *Clostridium difficile* and may have improved activity compared to deoxyactagardine B.

Susceptibility testing for *Clostridium difficile* strains was performed by two-fold serial antibiotic dilutions in Wilkins-Chalgren Anaerobe agar under anaerobic conditions. Vancomycin was included as a comparator drug. *C. difficile* cultures were inoculated onto pre-reduced Braziers (C.C.E.Y.) agar plates and grown at 37° C. for 48 hours under anaerobic conditions. Two to three colonies of the 48 hours cultures were inoculated into 5 ml of pre-reduced Schaedlers Broth and grown at 37° C. for 24 hours under anaerobic conditions. This culture was diluted with pre-reduced 0.9% NaCl to achieve the turbidity of the 0.5 McFarland standard and applied to the drug containing plates at a final inoculum of 105 cfu/spot. Drug-free growth control plates were included. The plates were incubated in the anaerobic chamber at 37° C. for 48 hours and examined for growth. The MIC was the lowest concentration of drug that completely inhibited growth or caused markedly reduction of growth as compared to growth on the drug-free plates.

TABLE 3

MIC data (μg/ml) for deoxyactagardine B (DAB), and derivatives thereof.

| C. diff strain | DAB | Eg 3 (p = 2) | Eg 5 (p = 3) | Eg 6 (p = 5) | Eg 1 (p = 7) | Eg7 (p = 9) | Eg8 (p = 12) |
|---|---|---|---|---|---|---|---|
| 37779 | 4 | 2, 2 | 1, 1 | 2, 2 | 1, 0.5 | 2, 1 | 1, 2 |
|  |  | 2, 2 | 1, 1 |  | 1, 1 |  | 1, 1 |
|  |  | 2, 1 | 1, 1 |  | 1, 1 |  |  |
|  |  |  | 2, 2 |  | 1, 1 |  |  |
| 19126 | 4 | 2, 1 | 2, 2 | 1, 1 | 1, 1 | 2, 1 | 1, 1 |
|  |  | 1, 2 | 1, 1 |  | 0.5, 1 |  | 2, 2 |
|  |  | 1, 1 | 1, 1 |  | 1, 1 |  |  |
|  |  |  | 2, 2 |  | 1, 0.5 |  |  |
| B32 | 2 | 2, 2 | 2, 2 | 2, 2 | 1, 1 | 2, 2 | 2, 1 |
| E16 | 2 | 4, 2 | 1, 2 | 2, 2 | 1, 2 | 2, 2 | 2, 2 |
| P24 | 2 | 2, 2 | 2, 2 | 2, 2 | 1, 1 | 2, 1 | 2, 1 |
| 027SM | 2 | 2, 2 | 2, 2 | 2, 2 | 1, 1 | 2, 2 | 2, 2 |
| P62 | 2 | 2, 2 | 2, 2 | 2, 2 | 2, 1 | 2, 2 | 2, 2 |
| E101 | 2 | 2, 2 | 2, 2 | 2, 2 | 1, 1 | 2, 2 | 2, 2 |
| 027Can | 4 | 2, 2 | 1, 1 | 2, 1 | 0.5, 0.5 | 0.5 | 1, 1 |
|  |  | 1, 2 | 0.5, 0, 5 |  | 0.5, 0.5 | 1, 1 | 1, 1 |
|  |  | 0.5 | 1, 0.5 |  | 1, 1 |  |  |
|  |  | 1 | 2, 2 |  | 1, 0.5 |  |  |
| E4 | 2 |  |  |  |  |  |  |
| P49 | 2 |  |  |  |  |  |  |
| P59 | 2 |  |  |  |  |  |  |
| 630 | 4 | 1, 1 | 1, 1 | 1, 1 | 0.5, 0.5 |  | 0.5, 0.5 |
|  |  | 1, 1 | 2, 2, | 1, 0.5 | 0.5, 1 |  | 1, 1 |
|  |  | 1, 1 | 1, 1 | 1, 1 | 1, 1 |  |  |
|  |  |  |  |  | 1, 1 | 1, 1 |  |

(The lower the value of the result the greater the activity of the test compound.)

Example 10

Stability of Type-B Lantibiotics in Intestinal Fluid

The lantibiotic-based compounds provided herein may have increased stability to enzymatic degradation compared to type-A lantibiotics, such as nisin. Particularly, the compounds may have improved stability to intestinal juices compared to type-A lantibiotics.

Nisin and the compound of Example 1 were tested for their susceptibility towards enzymatic digestion in the intestine using a simulated intestinal fluid (SIF). The SIF was based on the standard USP solutions for simulated intestinal fluids and its activity was confirmed against Bovine Serum Albumin (Hilger et al, *Clin. Exp. Immunol.* 2001, 123, 387-94). The compounds were incubated in SIF at 37° C. and their concentrations quantified by analytical HPLC (UV detection at 210 nm using the conditions outline in Table 1).

Figure 1:
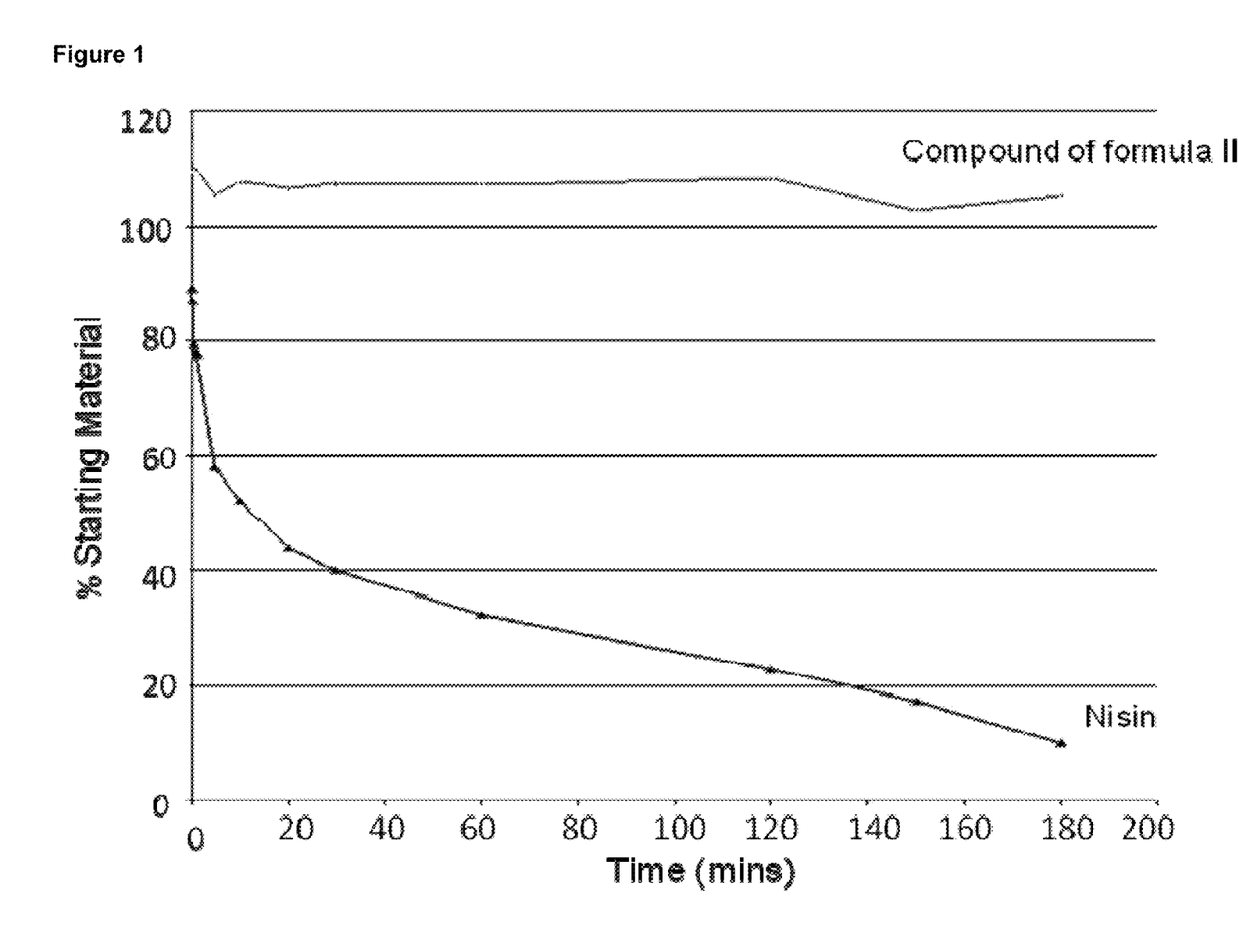
FIG. 1 shows the susceptibility to enzymic digestion of nisin and a deoxyactagardine B derivative.

FIG. 1 shows that nisin was rapidly degraded in SIF with a half-life of approximately 15 to 20 minutes. The rapid degradation of nisin in this medium supports the observation that the clinical utility of nisin for the treatment of colonic infections is very limited unless the compound can be protected from degradative enzymes by means of careful formulation.

FIG. 1 also shows that the compound of Example 1 is essentially stable in SIF and likely to have suitable stability for treating colonic *C. difficile* infections.

Example 11

Figure 2:
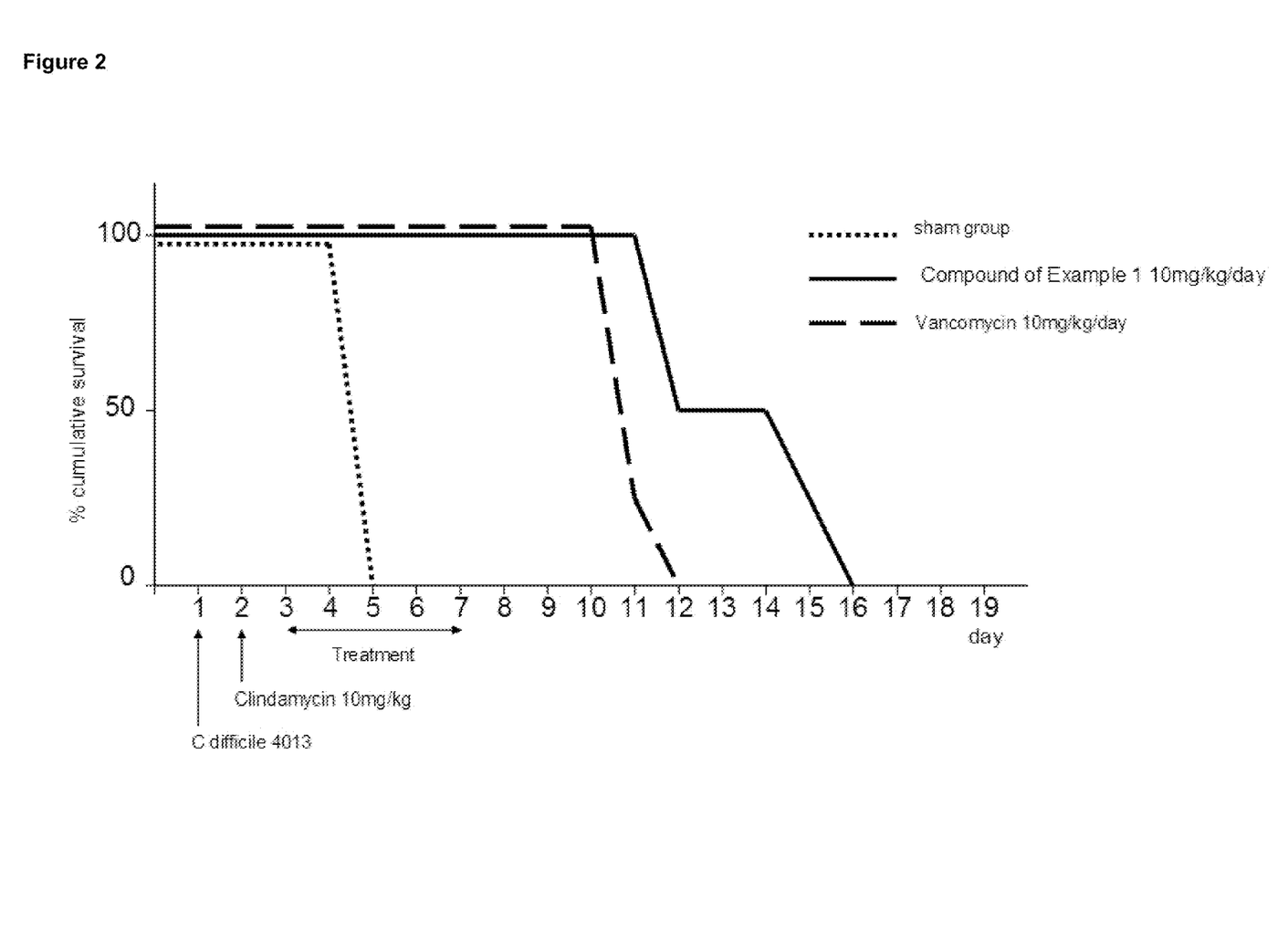
FIG. 2 shows the results of an in vivo model for *C. difficile*.

In Vivo Efficacy of Type-B Antibiotics in the Hamster Model of *C. difficile* Associated Cecitis The in vivo efficacy of the compounds of the invention in the treatment of *C. difficile* infections was evaluated in the standard animal model for CDAD, clindamycin induced cecitis in the hamster. The results are summarised in FIG. 2.

Groups of 6 animals were dosed with approximately $10^7$ cells of *C. difficile* strain 4013 and 24 hours later with a subcutaneous dose of 10 mg/kg clindamycin phosphate. After a further 24 hours, the groups were then treated either with vehicle, vancomycin or with the compound of Example 1 three times daily at 10 mg/kg/day.

The procedure as described induced a *C. difficile* infection in the test animals, from which all animals treated only with vehicle died within 3 days. In contrast, all animals treated with vancomycin or the DAB derivative survived for the duration of the entire 5-day dosing period, demonstrating the protective effects of these compounds.

Example 12

ADME in the Rat Model

Figure 3:
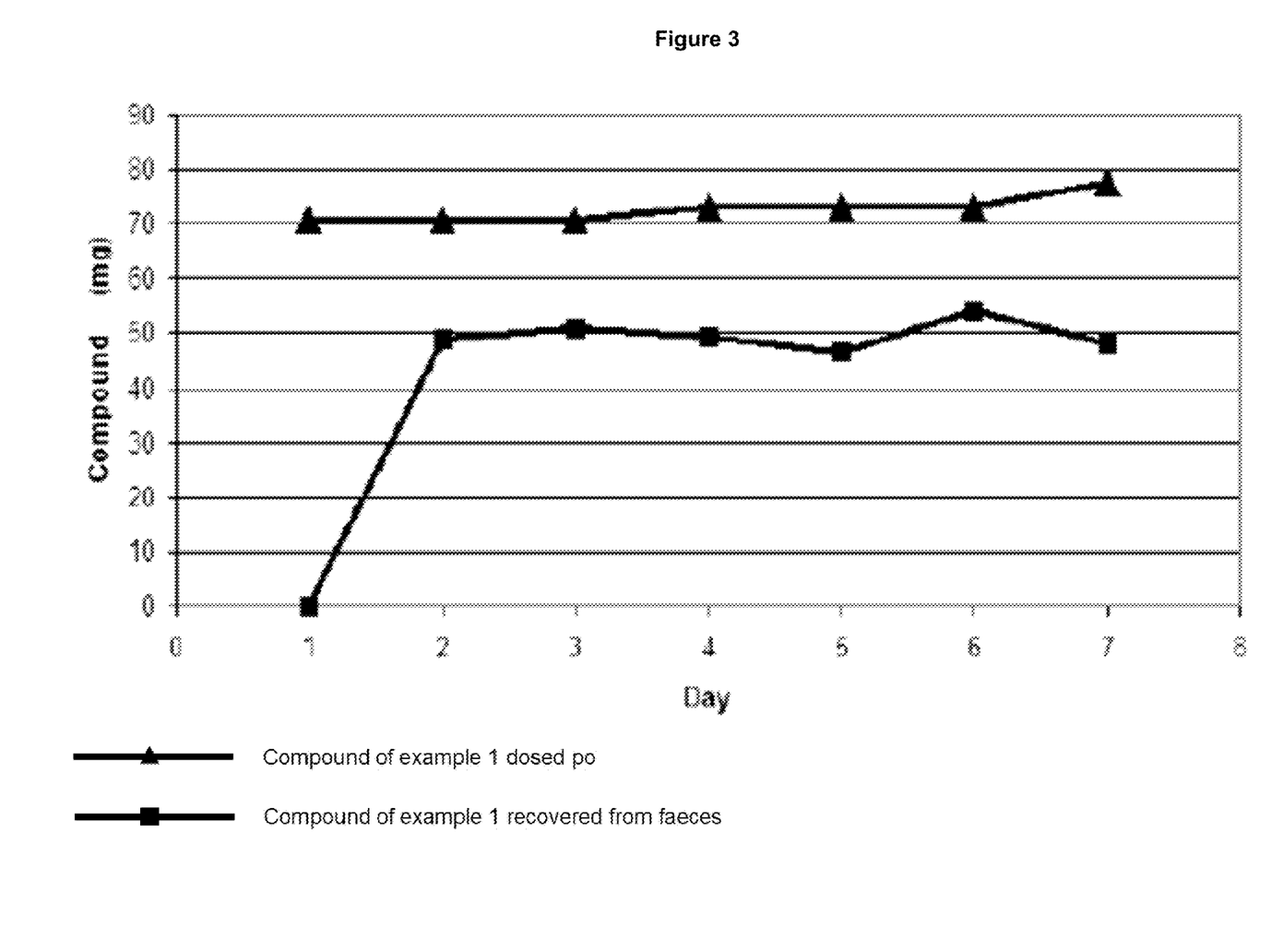
FIG. 3 shows the amount of compounds recovered after oral administration.

The compound of Example 1 was dosed orally to rats for 7 days and recovered from the faeces by extraction with methanol. FIG. 3 shows the amount of material recovered with respect to the amount administered to the rat. Whilst the amount of material recovered depends on the number of extractions, the data show that at least 60 to 70% of the compound of Example 1 can be recovered unchanged after its passage through the GI tract and that the compound of Example 1 can reach high concentrations in the colon.

Example 13

Toxicology in the Rat Model

The compound of Example 1 was tested in a 7-day toxicity experiment in a rat model. One study used 50 mg/kg/day of material administered intravenously for 7 days. The other study used 200 mg/kg/day of material administered orally for 7 days. Both the intravenous and oral doses significantly exceed the anticipated clinical dose level (around 3-30 mg/kg/day by oral dosing). No significant toxicological effects were observed during the experiment and necropsy revealed no organ damage.

The compound of Example 1 was tolerated without obvious signs of toxicity at 50 mg/kg/day orally in the Syrian hamster.

The invention claimed is:

1. A compound deoxyactagardine B (7-amino-1-heptylamide monocarboxamide), and pharmaceutically acceptable salts thereof.

2. A pharmaceutical composition comprising a compound according to claim 1, and a pharmaceutically acceptable excipient.

3. A composition according to claim 2, for oral administration.

4. A composition according to claim 2, for parenteral administration.

* * * * *